United States Patent
Criscuolo

(10) Patent No.: US 7,963,975 B2
(45) Date of Patent: Jun. 21, 2011

(54) BALLOON DISSECTOR WITH BALLOON TIP CANNULA

(75) Inventor: Christopher J. Criscuolo, Branford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 1113 days.

(21) Appl. No.: 10/842,101

(22) Filed: May 10, 2004

(65) Prior Publication Data

US 2005/0004592 A1    Jan. 6, 2005

Related U.S. Application Data

(60) Provisional application No. 60/468,919, filed on May 8, 2003.

(51) Int. Cl.
*A61B 17/00*    (2006.01)

(52) U.S. Cl. ........................................ 606/190

(58) Field of Classification Search .................. 606/170, 606/190, 191, 198
See application file for complete search history.

(56) References Cited

U.S. PATENT DOCUMENTS

| | | | |
|---|---|---|---|
| 397,060 | A | 1/1889 | Knapp |
| 512,456 | A | 9/1894 | Sadikova |
| 1,213,005 | A | 1/1917 | Pillsbury |
| 2,936,760 | A | 5/1960 | Gants |
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari et al. |
| 3,713,447 | A | 1/1973 | Adair |
| 3,774,596 | A | 11/1973 | Cook |
| 3,800,788 | A | 4/1974 | White |
| 3,882,852 | A | 5/1975 | Sinnreich |
| 3,961,632 | A * | 6/1976 | Moossun ................ 604/528 |
| RE29,207 | E | 5/1977 | Bolduc et al. |
| 4,083,369 | A | 4/1978 | Sinnreich |
| 4,217,889 | A | 8/1980 | Radovan et al. |
| 4,243,050 | A | 1/1981 | Littleford |
| 4,276,874 | A | 7/1981 | Wolvek et al. |
| 4,312,353 | A | 1/1982 | Shahbabian |
| 4,345,606 | A | 8/1982 | Littleford |
| 4,411,654 | A | 10/1983 | Boarini et al. |
| 4,490,137 | A | 12/1984 | Moukheibir |

(Continued)

FOREIGN PATENT DOCUMENTS

EP    0 480 653 A1    4/1992

(Continued)

OTHER PUBLICATIONS

European Search Report for EP 03770656.1 date of completion is Feb. 21, 2007 (6 pages).

*Primary Examiner* — Ryan J Severson

(57) ABSTRACT

There are disclosed various embodiments of a combined balloon dissector with balloon tip cannula which are provided to facilitate forming an anatomical space within the body, such as, for example, an anatomical space in the abdominal cavity or extraperitoneal space for facilitating hernia repair surgeries. The combined balloon dissectors with cannula generally include a cannula assembly for anchoring the device to the abdominal wall and a dissector assembly having a dissection balloon at a distal end for separating tissue layers and forming an anatomical space. Various combinations of valve ports and sub-assemblies are disclosed for providing inflation fluid to the balloon tip cannula, and inflation fluid for the dissection balloon.

14 Claims, 11 Drawing Sheets

U.S. PATENT DOCUMENTS

| | | | |
|---|---|---|---|
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,865,593 A | 9/1989 | Ogawa et al. |
| 4,869,717 A | 9/1989 | Adair |
| 4,888,000 A | 12/1989 | McQuilkin et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A * | 9/1992 | Castillenti ............... 604/164.04 |
| 5,147,374 A | 9/1992 | Fernandez |
| 5,158,545 A | 10/1992 | Trudell et al. |
| 5,159,925 A | 11/1992 | Neuwirth et al. |
| 5,163,949 A * | 11/1992 | Bonutti ......................... 606/192 |
| 5,176,692 A | 1/1993 | Wilk et al. |
| 5,176,697 A | 1/1993 | Hasson et al. |
| 5,183,463 A * | 2/1993 | Debbas ....................... 604/98.01 |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A * | 6/1993 | Deniega et al. .......... 604/164.09 |
| 5,222,970 A | 6/1993 | Reeves |
| 5,226,890 A | 7/1993 | Ianniruberto et al. |
| 5,232,446 A | 8/1993 | Arney |
| 5,234,454 A * | 8/1993 | Bangs .......................... 606/191 |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,468,248 A | 11/1995 | Chin et al. |
| 5,514,153 A | 5/1996 | Bonutti |
| 5,540,658 A | 7/1996 | Evans et al. |
| 5,540,711 A | 7/1996 | Kieturakis et al. |
| 5,607,443 A | 3/1997 | Kieturakis et al. |
| 5,667,479 A | 9/1997 | Kieturakis |
| 5,707,382 A | 1/1998 | Sierocuk et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,772,680 A | 6/1998 | Kieturakis et al. |
| 5,779,728 A | 7/1998 | Lunsford et al. |
| 5,797,947 A | 8/1998 | Mollenauer |
| 5,810,867 A * | 9/1998 | Zarbatany et al. ............ 606/191 |
| 5,814,060 A | 9/1998 | Fogarty et al. |
| 5,836,913 A | 11/1998 | Orth et al. |
| 5,836,961 A | 11/1998 | Kieturakis et al. |
| 5,893,866 A | 4/1999 | Co et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,272 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 * | 9/2004 | Cioanta et al. ........... 604/103.01 |

FOREIGN PATENT DOCUMENTS

| | | |
|---|---|---|
| EP | 0 610 099 | 8/1994 |
| EP | 0 880 939 A | 12/1998 |
| WO | WO 92/06638 A1 | 4/1992 |
| WO | WO 97/21461 A | 6/1997 |
| WO | WO 99/12602 | 3/1999 |
| WO | WO 01/26724 | 4/2001 |
| WO | WO 02/96307 A2 | 5/2002 |
| WO | WO 2004/032756 | 4/2004 |

* cited by examiner

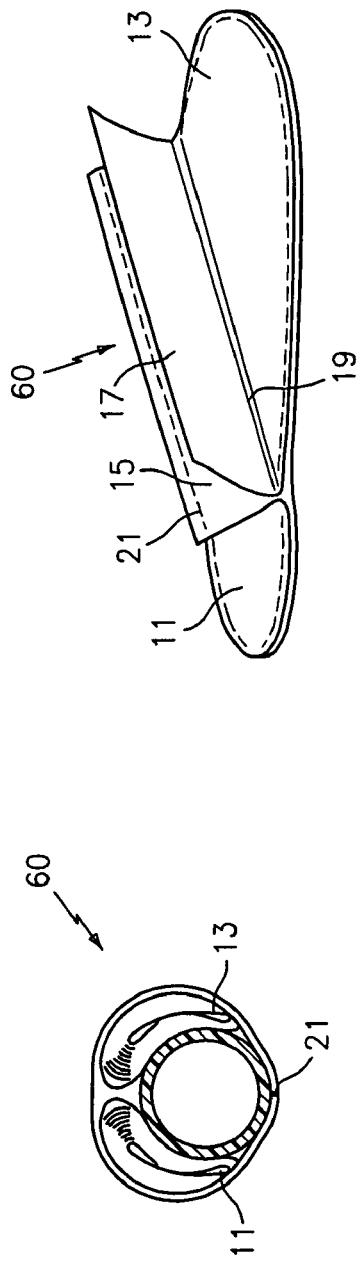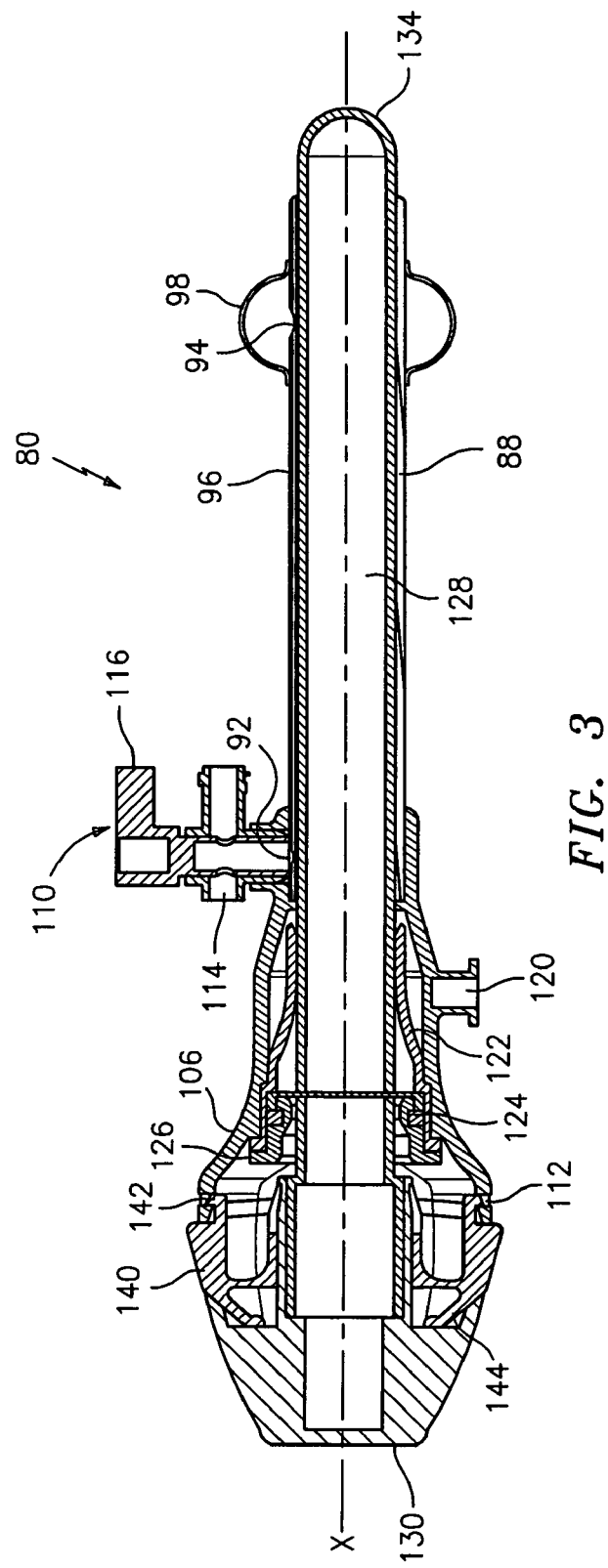

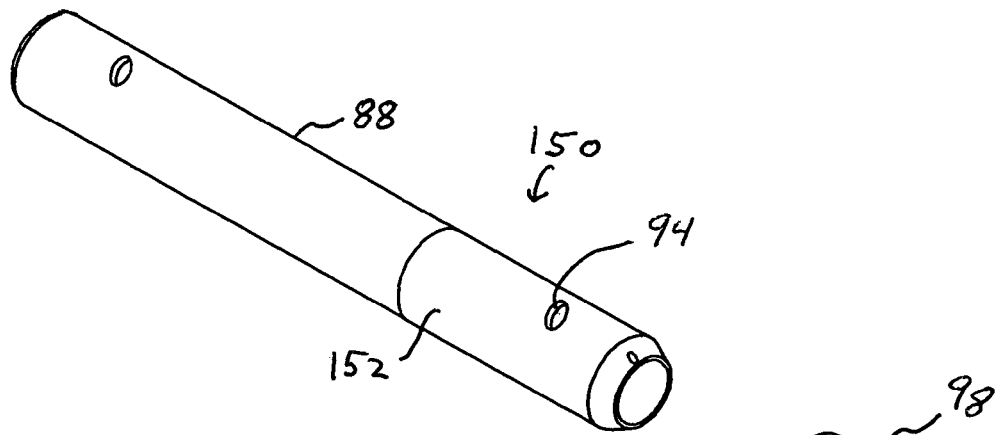
FIG. 4A
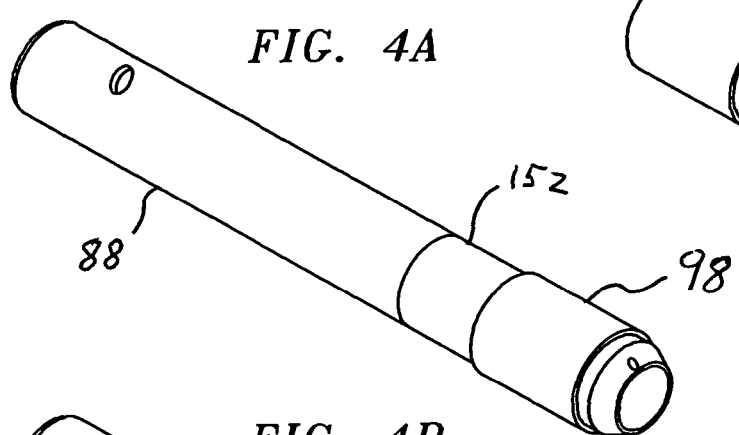
FIG. 4B
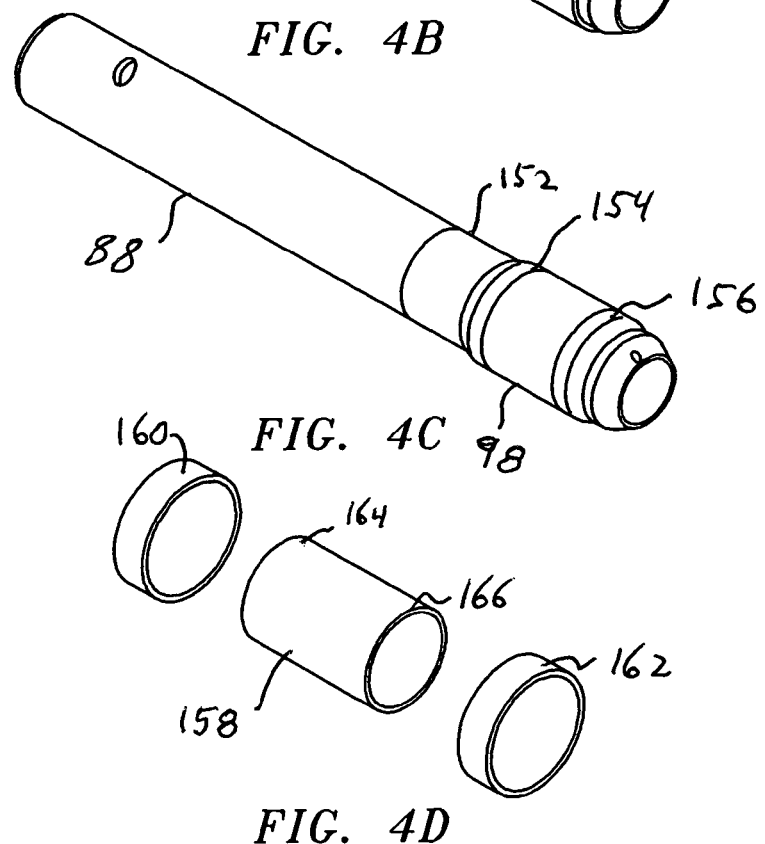
FIG. 4C
FIG. 4D

BALLOON DISSECTOR WITH BALLOON TIP CANNULA

CROSS-REFERENCE TO RELATED APPLICATIONS

This application claims the benefit of U.S. Provisional Application Ser. No. 60/468,919, filed May 8, 2003, and U.S. patent application Ser. No. 10/680,368, filed Oct. 6, 2003, the disclosures of which are hereby incorporated by reference.

BACKGROUND

1. Technical Field

The technical field relates to balloon dissectors for forming an anatomical space within a body, to cannulas having balloon anchors, and to apparatus having a combined balloon dissector and balloon tip cannula.

2. Background of Related Art

During various surgeries, it is necessary to dissect tissue layers to form an anatomical space within which surgical instruments may be manipulated. For example, in hernia repair surgery, it is necessary to form an anatomical operative cavity within the extraperitoneal space in order to dissect fascia tissue layers and access the hernia site. Various balloon dissectors are known for performing the tissue dissection procedure used in hernia repair surgery. These generally include a single device having a dissection balloon formed on the distal end of a tube and an inflation port formed on the proximal end of the tube. The balloon dissector is inserted into an incision and the balloon is inflated for dissection. After dissection and after removing the balloon dissector from the incision, a cannula is inserted into the incision and used to insufflate while forming an access passageway for the introduction of surgical instruments into the anatomical space.

While the currently known tissue dissection devices and cannulas are useful, improvements are desirable. It would be beneficial to have a balloon dissector device combined with a balloon tip cannula.

SUMMARY

There is disclosed a balloon dissector assembly for creating an anatomical space within a body and a balloon tip cannula assembly for providing an access port into the body. The balloon dissector assembly and the balloon tip cannula assembly can be used separately as stand alone instruments or, preferably, as a combined balloon dissector and balloon tip cannula. Notably components on both devices allow them to be easily combined.

In an aspect of the present invention, a balloon dissector and balloon tip cannula assembly comprises: a balloon dissector including a dissector tube defining a passage and a dissection balloon having an interior and being affixed to a distal end of the dissector tube so that the passage and the interior communicate with one another; an obturator configured for insertion through the passage; a balloon tip cannula having a cannula tube receiving the balloon dissector, the cannula tube having a distal end and an anchoring balloon at the distal end; and an adapter having a dissection inflation port in communication with the passage for inflating the dissection balloon, an anchor inflation port in communication with the anchoring balloon, and an insufflation port in communication with the cannula tube.

In a further aspect of the present invention, a balloon dissector and balloon tip cannula assembly comprises: a balloon dissector including a dissector tube defining a passage and a dissection balloon having an interior and being affixed to a distal end of the dissector tube so that the passage and the interior communicate with one another; an obturator configured for insertion through the passage and into the interior of the dissection balloon; and a balloon tip cannula having a cannula tube receiving the balloon dissector, the cannula tube having a distal end and an anchoring balloon at the distal end.

In certain preferred embodiments, the balloon dissector has an inflation port arranged for providing inflation fluid to the passage. The balloon dissector may include latching structure to releasably retain the balloon tip cannula. Additionally or in the alternative, the balloon tip cannula may include latching structure to releasably retain the balloon dissector.

In certain embodiments, the balloon dissector has a removable shroud arranged to cooperate with the latching structure on the balloon tip cannula. In certain preferred embodiments, an inner surface of the dissector tube and an outer surface of the obturator defines an inflation lumen therebetween for inflating the dissection balloon. The balloon dissector may also include a dissector inflation valve so that the inflation lumen communicates between the dissector inflation valve and the dissection balloon.

In certain preferred embodiments, the assembly includes a separable securing sleeve arranged to retain the dissection balloon in an initial collapsed configuration.

In a further aspect of the present invention, a balloon dissector assembly, comprises: a balloon dissector including a dissector tube defining a passage and a dissection balloon having an interior and being affixed to a distal end of the dissector tube so that the passage and the interior communicate with one another; and an obturator configured for insertion through the passage and being arranged with the dissector tube so as to form an inflation lumen communicating with the interior of the balloon.

In a further aspect of the present invention, a balloon dissector assembly comprises: a balloon dissector including a dissector tube defining a passage and a dissection balloon having an interior and being affixed to a distal end of the dissector tube so that the passage and the interior communicate with one another and so that the dissection balloon extends from the distal end of the dissector tube; and an obturator configured for insertion through the passage and into the interior of the dissection balloon so that the dissection balloon is supported on the obturator.

In certain preferred embodiments, the assembly includes a separable securing sleeve arranged to retain the dissection balloon in an initial collapsed configuration on the obturator. The balloon dissector may also have an inflation port arranged for providing inflation fluid to the passage. The inflation fluid is desirably communicated to the dissection balloon. As the balloon starts to expand, a weakened region of the sleeve separates to release the dissection balloon. The expanded dissection balloon preferably forces tissue layers apart along natural tissue planes to create an anatomical space.

In certain preferred embodiments, an inner surface of the dissector tube and an outer surface of the obturator defines an inflation lumen therebetween. A proximal end of the balloon dissector desirably includes an orifice in communication with the passage so that upon removal of the obturator from the dissector tube, the dissection balloon deflates. The balloon dissector desirably includes a dissector inflation valve and the inflation lumen communicates between the dissector inflation valve and the dissection balloon.

In a further aspect of the present invention, a method of creating an anatomical space within a body for use in surgery comprises forming an incision in the body and inserting a balloon dissector assembly through the incision to a desired position. The balloon dissector assembly comprises: i) a balloon dissector including a dissector tube defining a passage and a dissection balloon having an interior and being affixed to a distal end of the dissector tube so that the passage and the interior communicate with one another; and ii) an obturator configured for insertion through the passage and being arranged with the dissector tube so as to form an inflation lumen communicating with the interior of the balloon. The method includes: inflating the dissection balloon by introducing inflation fluid through the inflation lumen, so as to force tissue layers apart along natural tissue planes to create an anatomical space; and deflating the balloon.

In a further aspect of the present invention, a method of creating an anatomical space within a body for use in surgery comprises forming an incision in the body and inserting a balloon dissector assembly through the incision to a desired position. The balloon dissector assembly comprises: i) a balloon dissector including a dissector tube defining a passage and a dissection balloon having an interior and being affixed to a distal end of the dissector tube so that the passage and the interior communicate with one another and so that the dissection balloon extends from the distal end of the dissector tube; and ii) an obturator configured for insertion through the passage and into the interior of the balloon so that the dissection balloon is supported on the obturator. The method includes the step of inserting including tunneling through tissue with the obturator; inflating the dissection balloon so as to force tissue layers apart along natural tissue planes to create an anatomical space; and deflating the balloon.

In certain preferred embodiments, the obturator and dissector tube define an inflation lumen therebetween and the method includes introducing inflation fluid into the inflation lumen so as to inflate the dissection balloon. The method may include removing the obturator before the step of inflating and inserting an instrument into the passage. The instrument may comprise an endoscope.

In certain preferred embodiments, the obturator is removed after the step of inflating so as to deflate the dissection balloon. The balloon dissection assembly may include a separable securing sleeve arranged to retain the dissection balloon in an initial collapsed configuration and the step of inflating the dissection balloon may include separating the sleeve.

In certain preferred embodiments, the balloon dissector assembly is inserted into the abdomen and a hernia in the abdomen is repaired.

In another aspect of the present invention, an assembly for providing subcutaneous access to a body cavity comprises: a balloon tip cannula having a cannula tube and an anchoring balloon on a distal end of the cannula tube, the balloon tip cannula having an anchor inflation port and a lumen in communication with the anchoring balloon, the balloon tip cannula having an insufflation port for providing insufflation fluid to the body cavity; an obturator received in the cannula tube; the balloon tip cannula having an adapter on a proximal end thereof, the adapter and the obturator being arranged for connecting the obturator and the balloon tip cannula, the adapter having at least one seal disposed within the adapter and being arranged to attach to a device to be received in the cannula tube after the obturator is removed from the cannula tube.

There is disclosed a novel method of securing a balloon anchor to a tube which includes the steps of dipping a selective region of the tube in a suitable material, for example, urethane, and positioning the inflatable balloon anchor about the selective region. Thereafter, opposed ends of the inflatable balloon anchor may be subjected to a thermal weld to weld the opposed ends to the coated selective region. There may be additionally provided a silicone sleeve positionable over the inflatable balloon anchor and secured thereto by means of heat shrink rings applied to opposed ends of the silicone sleeve.

In certain preferred embodiments, the cannula tube has a wall and a lumen is defined in the wall, the lumen communicating with the anchor inflation port and the anchoring balloon. A skin seal may be movably mounted on the cannula tube. The skin seal may include structure for securing the skin seal at a desired longitudinal location on the elongated tube.

In certain preferred embodiments, the at least one seal includes a first seal for sealing the cannula tube in the absence of an instrument being received within the cannula tube. The at least one seal may also include a second seal for sealing the cannula tube when the instrument is received within the cannula tube. The insufflation port is preferably located distally of the at least one seal.

In certain preferred embodiments, the device comprises the obturator and in others, the device comprises a dissector.

The obturator may include an elongate body configured to fit within the cannula tube so as to extend partially out the distal end of the cannula tube.

In another aspect of the present invention, a method of creating an anatomical space within an abdomen and providing subcutaneous access to a body cavity within the abdomen comprises: creating the anatomical space using a dissector inserted into an incision in the body, the dissector being connected to a balloon tip cannula; inserting the balloon tip cannula through the incision, the balloon tip cannula comprising a cannula tube with an anchoring balloon on a distal end thereof and an adapter on a proximal end thereof, the adapter being arranged for connecting with the dissector; detaching the balloon tip cannula from the dissector; inflating the anchoring balloon; engaging the anchoring balloon against an inner surface of the body cavity; sliding the skin seal distally against an outer surface of the body cavity; and removing the dissector and introducing insufflation fluid into the body cavity. Desirably, the step of detaching is performed before the step of inserting the balloon tip cannula and the balloon tip cannula is advanced distally on the dissector. The method may include removing an obturator from the balloon tip cannula and the dissector may be inserted in the balloon tip cannula.

The skin seal may be secured in place. An endoscope may be inserted into the balloon tip cannula after the step of removing the dissector. The balloon tip cannula desirably includes an anchor inflation port in communication with the anchoring balloon and the method may include the step of deflating the anchoring balloon by opening the anchor inflation port. In a further aspect of the present invention, a method of dissecting tissue and providing subcutaneous access to a body cavity comprises introducing a balloon dissector and balloon tip cannula assembly into an incision. The balloon dissector and balloon tip cannula assembly comprises: i) a balloon dissector including a dissector tube defining a passage and a dissection balloon having an interior and being affixed to a distal end of the dissector tube so that the passage and the interior communicate with one another, the balloon dissector having an inflation port arranged for providing inflation fluid to the passage; ii) a first obturator configured for insertion through the passage and into the interior of the dissection balloon; and iii) a balloon tip cannula having a cannula tube and an anchoring balloon on a distal end of the cannula tube. The method includes: inserting the balloon dissector and balloon tip cannula assembly into the body to a desired location; inflating the dissection balloon so as to dissect tissue along natural tissue planes; deflating the dissection balloon; advancing a distal tip of the balloon tip cannula through the incision to position the anchoring balloon within the body cavity; inflating the anchoring balloon and advancing the skin seal against the outer surface of the body; removing the balloon dissector and first obturator from the balloon tip cannula; and introducing insufflation fluid into the body.

In certain preferred embodiments, the balloon tip cannula has a second obturator and the method includes the step of assembling the balloon tip cannula and balloon dissector by removing the second obturator and inserting the balloon dissector into the balloon tip cannula. Latching structure on the balloon dissector may be engaged with the balloon tip cannula. The first obturator is removed before the step of deflating and an endoscope is inserted into the dissector tube. The method may include releasing the latching structure from the balloon tip cannula.

The skin seal is desirably secured against the outer surface of the body. Desirably, the method includes deflating the anchoring balloon. The balloon tip cannula may be removed from the body.

BRIEF DESCRIPTION OF THE DRAWINGS

Preferred embodiments of the presently disclosed balloon dissector and balloon tip cannula are described herein with reference to the drawings, wherein:

FIG. 2A is a cross-sectional view taken along line 2A-2A in FIG. 1;

FIG. 2B is a perspective view of a balloon in accordance with the embodiment of FIGS. 1-2A.

FIG. 3 is a cross-sectional side view of a balloon tip cannula assembly according to another embodiment of the present invention;

FIG. 4A is a perspective view of the elongated tube of the balloon tip cannula and inflatable balloon anchor;

FIG. 4B is a perspective view of the elongated tube of the balloon tip cannula with the inflatable balloon anchor positioned over a distal end;

FIG. 4C is a view similar to that of FIG. 4B with opposed ends of the inflatable balloon anchor welded to the elongated tube;

FIG. 4D is a perspective view of a silicone sleeve and heat shrink tubing for securement over the inflatable balloon anchor;

DETAILED DESCRIPTION OF PREFERRED EMBODIMENTS

Figure 1:
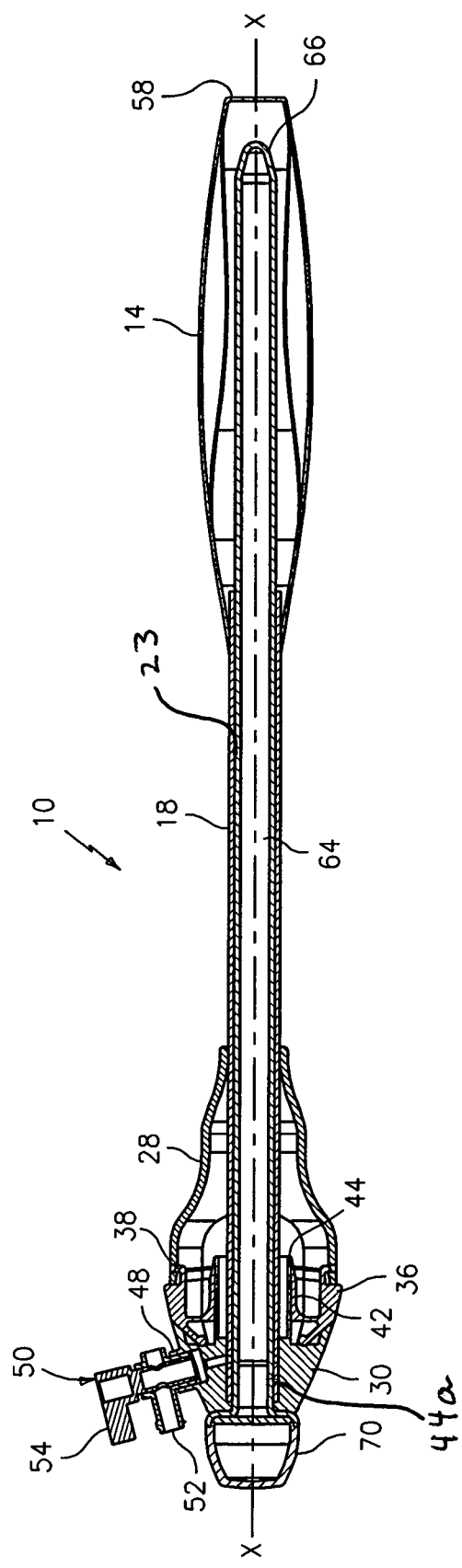
FIG. 1 is a cross-sectional side view of a balloon dissector assembly according to an embodiment of the present invention.

Preferred embodiments of the presently disclosed balloon dissector assembly, balloon tip cannula assembly and the combined balloon dissector with balloon tip cannula will now be described in detail with reference to the drawings, in which like reference numerals designate identical or corresponding elements in each of the several views. As used herein, the term "distal" refers to that portion of the instruments, or component thereof, which is further from the user while the term "proximal" refers to that portion of the instrument, or component, thereof which is closer to the user.

Figure 2:
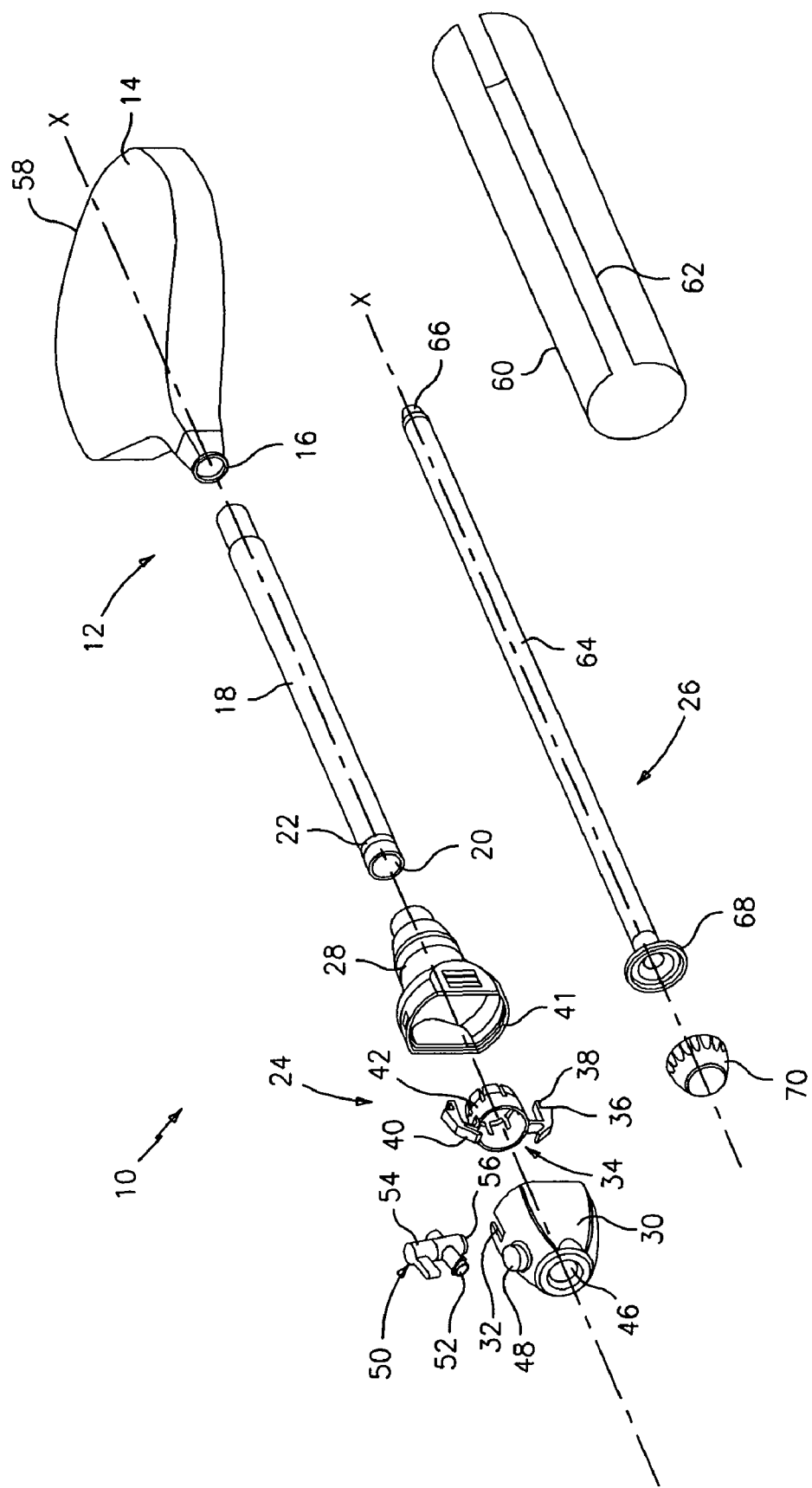
FIG. 2 is an exploded perspective view of the balloon dissector assembly in accordance with the embodiment of FIG. 1.

Referring to FIGS. 1 and 2, a balloon dissector assembly 10 according to an embodiment of the present invention is shown. Balloon dissector assembly 10 generally has a longitudinal axis-X and includes a balloon dissector 12 having an adapter assembly 24 and an obturator assembly 26. Balloon dissector assembly 10 includes a dissection balloon 14 configured and adapted for inflating in order to separate layers of tissue to form an anatomic space within the body of a patient. An inflation aperture 16 is located in the proximal region of dissection balloon 14 and is dimensioned to receive and be affixed to a distal end of a dissector tube 18. Dissector tube 18 is an elongated tubular structure having open proximal and distal ends defining an access passage 20 therebetween. An inflation port 22 is located at a proximal end of dissector tube 18 and provides a communicative channel between the passage 20 and a source of inflation pressure.

It is further envisioned that dissection balloon 14 may be manufactured from a material wherein the distal region 58 includes a substantially transparent section, or window, thereby allowing visual access to the dissected space. Additionally or alternatively, dissection balloon 14 may be manufactured from a material that is substantially transparent, also allowing visual access to the dissected space. As inflation pressure is applied, dissection balloon 14 desirably expands to a predetermined shape and size. Different shapes and sizes are envisioned with the surgical procedure to be performed determining which shape and size is selected. The dissection balloon can be elastic in all directions, relatively inelastic, selectively elastic in a particular direction such as in its height.

Referring for the moment to FIGS. 2A and 2B, a sleeve cover 60 is provided around dissection balloon 14 to retain dissection balloon 14 in a collapsed condition during insertion into the body and prior to inflation. Sleeve cover 60 may be affixed to dissection balloon 14, attached to dissector tube 18 or movably mounted with respect thereto. Sleeve cover 60 includes a longitudinal weakened perforated region 21 such that upon inflation of dissection balloon 14 the sleeve separates along the perforations and releases dissection balloon 14. In certain preferred embodiments, the dissection balloon 14 has marginal ends 11 and 13 that are rolled inwardly toward axis X and secured using the sleeve cover 60. The sleeve cover is heat sealed at 19 to the material of the balloon in the form of two flaps 15, 17. After the marginal edges 11 and 13 are folded or rolled, the flaps of the sleeve cover 60 are extended around the rolled balloon and the flaps are heat sealed to one another. Preformed perforation 21 in one of the flaps enables the sleeve cover 60 to separate upon inflation of the balloon.

Prior art dissection balloons are generally disposed substantially orthogonal to the longitudinal axis of the device wherein their initial inflation motion aligns them with the longitudinal axis, possibly increasing unintended tissue damage. In the present embodiment, the balloon desirably unrolls or unfolds in a lateral direction.

An adapter assembly 24 is configured for attachment to the proximal end of dissector tube 18 and generally includes a shroud 28 and an end cap 30 having a latching adaptor 34 attached to end cap 30, as best seen in FIG. 2. Located in a distal region of adapter assembly 24, the removable shroud 28 is dimensioned for surrounding the proximal end of dissector tube 18. Shroud 28 is preferably configured in a generally frusto-conical shape wherein a narrow portion surrounds dissector tube 18 and a wider portion is adapted for receiving latching adapter 34. Latching adapter 34 includes a pair of opposed arms 36. Each arm 36 is generally flexible and biased to spring return to its starting position. Furthermore, each arm 36 includes a distal hook 38 and a proximal lever 40. By actuating levers 40 towards longitudinal axis-X, arms 36 pivot about an attachment point causing each hook 38 to rotate generally about its attachment point. When latching adapter 34 is attached to shroud 28, hooks 38 are in releasable engagement with recesses 41 formed in shroud 28.

The distal end of latching adapter 34 includes a plurality of tabs 42 and are configured for affixing latching adapter 34 to an inner wall 44 of end cap 30, as best seen in FIG. 1. Inner wall 44a of end cap 30 surrounds and is affixed to a proximal end of dissector tube 18. A central opening through latching adapter 34 is provided to receive different devices, such as, for example, an obturator or an endoscope, which can be received through the end cap 30, latching adaptor 34, shroud 28 and tube 18, and position these devices within balloon tip dissector assembly 10. In certain preferred embodiments, the central opening is dimensioned for slidingly receiving devices generally having a diameter of between about 5 and about 10 millimeters, although embodiments for accommodating smaller and larger sizes are contemplated.

The adapter assembly 24 may comprise one or more parts. In other embodiments, any of the end cap 30, latching adapter 34, and shroud 28 may be combined in a unitary part. Preferably, shroud 28 is ergonomically designed for use by a surgeon and configured to give the balloon dissector a streamlined look. In a preferred embodiment, the end cap 30, latching adapter 34 and shroud 28 are combined in one integral part attached to a proximal end of the dissector tube 18.

An adapter orifice 46 and a connecting port 48 are located on end cap 30. Optimally, adapter orifice 46 is substantially circular, centrally located on end cap 30, and configured to receive devices therethrough. A diameter reducing device (not shown) may be included as well to accommodate devices having a diameter less than a given size. The reducing device would be attached to end cap 30 over adapter orifice 46 for engaging tubular surgical devices of differing sizes and providing a degree of stability for the surgical devices inserted through adapter orifice 46. Alternatively or additionally, the end cap 30 desirably includes a seal for maintaining fluid pressure within the dissection balloon when the obturator or scope is received in the inflation tube and through the end cap 30. The connecting port 48 is dimensioned for receiving a valve 50 in a sealing manner such that valve 50 is in fluid communication with connecting port 48.

A dissector inflation valve 50 is preferably located on a surface of end cap 30 that is readily accessible during a surgical procedure. When dissector inflation valve 50 is attached to end cap 30, valve port 52 is aligned and in fluid communication with inflation port 22 in dissector tube 18 and therefore in fluid communication with dissection balloon 14. Dissector inflation valve 50 also includes a valve handle 54 that is rotatably attached to dissector inflation valve 50 wherein internal valve ports (not shown) are configured to permit fluid flow between valve port 52 and inflation port 22.

In a preferred embodiment, dissector inflation valve 50 is a one-way check valve with a stopcock for inflating and deflating dissector balloon 14. In use, inflation pressure is applied to valve port 52 that is further communicated through the circumferential lumen of dissector tube 18 causing dissection balloon 14 to expand. Having a check-valve internal to dissector inflation valve 50 minimizes the loss of inflation pressure through dissector inflation valve 50 thereby allowing dissection balloon 14 to maintain its shape and inflation pressure. Advantageously, dissector inflation valve 50 includes a stopcock for releasing the inflation pressure. Including a stopcock with dissector inflation valve 50 allows the surgical personnel to have better control over the inflation and deflation of dissection balloon 14 since it is integrated into dissector inflation valve 50, and valve 50 is readily accessible to the surgical personnel. In other embodiments, a separate deflation device may be provided.

According to the present disclosure, obturator assembly 26 generally includes an obturator body 64 having a tip 66 that is generally conical in shape and is formed the distal end of the obturator body 64. Located at the proximal end of obturator body 64 is an obturator flange 68. An obturator cap 70 is affixed to obturator flange 68. Preferably, obturator cap 70 is ergonomically shaped for comfortable use by surgical personnel. In certain preferred embodiments, the obturator comprises a unitary part having an elongated body and a proximal end desirably ergonomically shaped for use by surgical personnel.

To assemble the balloon dissector assembly 10 prior to use, tip 66 of obturator assembly 26 is inserted through adapter orifice 46 and obturator assembly 26 is advanced distally along longitudinal axis-X. When the underside of obturator flange 68 abuts end cap 30, maximum longitudinal travel of obturator assembly 26 is accomplished. The obturator body 64 is sized so that the outer surface of obturator body 64 and the inner surface of dissector tube 18 form an inflation lumen 23 between valve port 52 and dissection balloon 14.

In order to inflate dissection balloon 14, a source of inflation pressure is releasably attached to valve port 52. Valve handle 54 is rotated to align the internal valve ports for fluid flow through dissector inflation valve 50. Pressurized fluid is introduced through valve port 52 and is communicated through dissector inflation valve 50, inflation port 22, and inflation lumen 23 to dissection balloon 14. In another alternative, the dissector tube 18 terminates at a location distal of the valve 50 and connecting port 48 and the inflation port 22 is eliminated. Examples of preferred inflation fluids include $CO_2$, saline solution, or other biocompatible fluids. The pressurized fluid causes dissection balloon 14 to expand. In a preferred embodiment, dissection balloon 14 is manufactured from a suitable biocompatible material. For example, the balloon may comprise a sheet having a thickness of about 2 mils, or 0.002 inches.

A method of use for balloon dissector assembly 10 as a stand alone device is disclosed. Alternatively, balloon dissector assembly 10 can be used with an access port or cannula in the manner described herein below. Balloon dissector assembly 10 is shown in an assembled state in FIG. 1. Typically, a suitably sized incision is made in the patient's skin. Next, the assembled balloon dissector assembly 10 is inserted into the incision using obturator 26 positioned within balloon dissector 12 to tunnel a passage beyond the point of incision, with the dissection balloon 14 supported on the obturator body 64. As balloon dissector assembly 10 is inserted, dissection balloon 14 is restrained by sleeve cover 60 and generally surrounds the distal region of obturator body 64 that extends beyond the distal end of dissector tube 18. Preferably, dissection balloon 14 is formed from a material that has sufficient strength to minimize damage to dissection balloon 14 during the tunneling process, but is also has a minimal surface resistance, thereby permitting ease of entrance of dissection balloon 14 into the incision and the surrounding soft tissue.

Inflation pressure is applied through valve port 52 from a suitable outside source and is communicated through dissector inflation valve 50 to dissection balloon 14. As pressure is applied, dissection balloon 14 expands and causes the perforated sleeve cover 60 to separate along perforations 21, or a weakness in the sleeve cover 60 material to break, so as to release dissection balloon 14. Dissection balloon 14 unrolls or unfolds laterally and expands vertically to a predetermined shape and size. The vertical expansion of dissection balloon dissects surrounding tissue along natural tissue planes. Once the desired space is created, dissection balloon 14 is deflated by operating the stopcock on valve 50 to release the pressure inside dissection balloon 14. Alternately, removal of obturator assembly 26 allows the inflation pressure to be relieved through the opening at adapter orifice 46.

Following removal of obturator assembly 26, other suitable configured surgical instruments, or devices may be inserted into dissector tube 18. One such example is an endoscope for viewing the dissected space wherein at least a portion of the dissection balloon 14 is substantially transparent for viewing the dissected space. In alternative embodiments, the obturator assembly 26 may be removed, either before or after the balloon dissector assembly 10 is introduced into the body, and the endoscope may be inserted into the dissector tube 18 prior to inflation of the dissection balloon. Desirably, the balloon dissector assembly 10 is removed after dissection and the dissected space is insufflated, as is known in the art.

Figure 4:
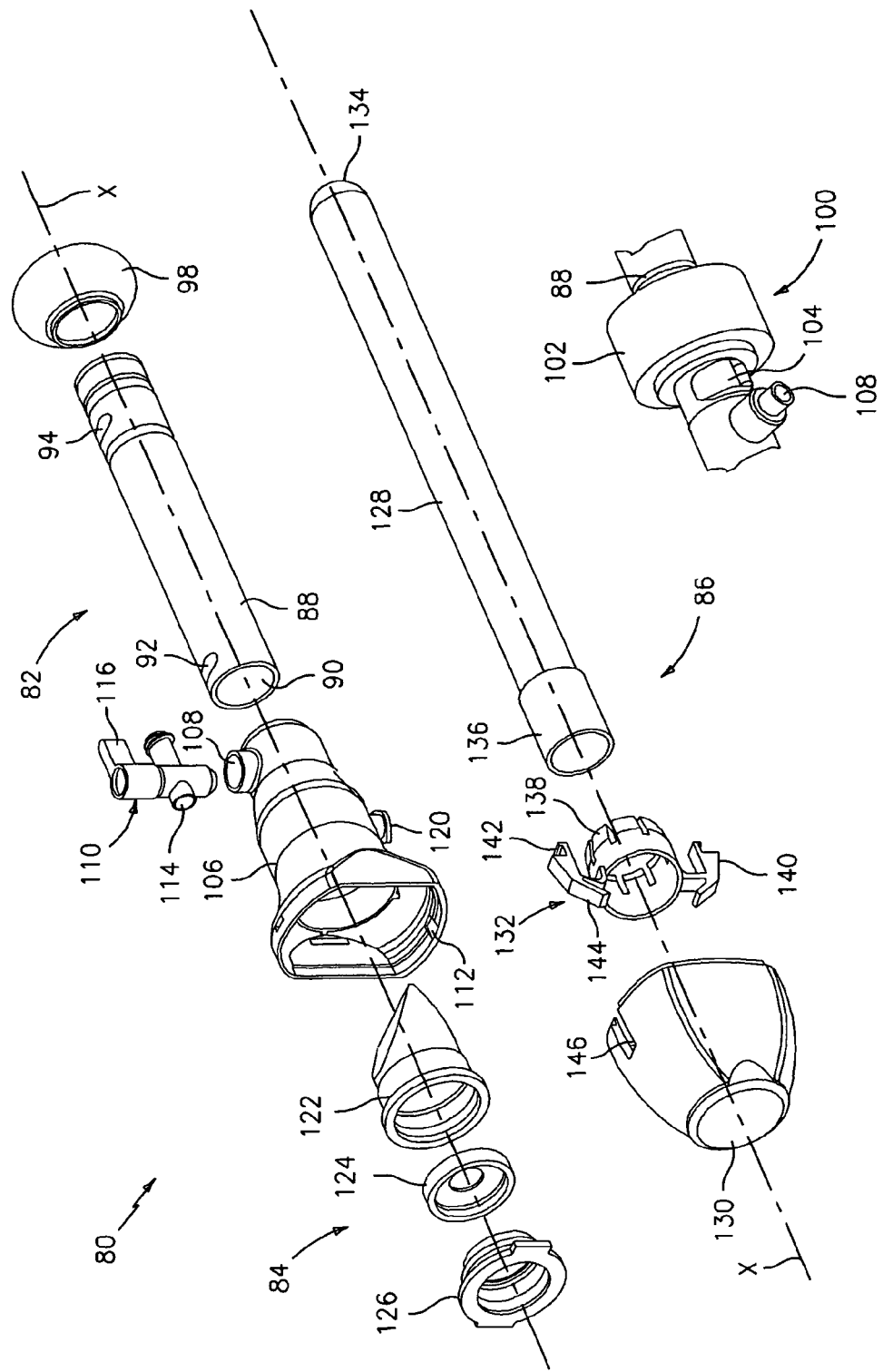
FIG. 4 is an exploded perspective view of the balloon tip cannula assembly in accordance with the embodiment of FIG. 3.

Referring now to FIGS. 3 and 4, there is disclosed a balloon tip cannula assembly 80 for use as an access port for use with various surgical instruments or in combination with balloon dissector assembly 10 as described in more detail hereinbelow. A balloon tip cannula assembly 80 generally includes a balloon tip cannula 82 having a seal assembly 84 and an obturator 86.

Balloon tip cannula 82 comprises an elongated tube 88 that is open at its proximal and distal ends defining an access lumen 90 for receipt of surgical instruments therethrough. A proximal lumen port 92 and a distal lumen port 94 are disposed on an outer surface of the cannula 88. Defined between the inner surface and the outer surface of tube 88 is an inflation lumen 96 extending along longitudinal axis-x and communicating with proximal and distal lumen ports 92, 94. An inflatable balloon anchor 98 is disposed in the distal region of tube 88. In a preferred embodiment, balloon anchor 98 has a generally toroidal shape, is located along tube 88, and encloses distal lumen port 94 in a substantially fluid-tight sealing manner. Further still, balloon anchor 98 is expandable to a predetermined size and shape.

Referring for the moment to FIGS. 4A to 4C, inflatable balloon anchor 98 is affixed to a distal end of elongated tube 88 in a novel manner. In order to prepare elongated tube 88 to receive inflatable balloon anchor 98, a selective region 150 of elongated tube 88 is dipped in a suitable material having characteristics sufficient for adhesion to inflatable balloon anchor 98. Preferably, selective region 150 is dipped in a urethane material to result in a urethane coating 152 over selective region 150. In order to attach inflatable balloon anchor 98 to elongated tube 88, inflatable balloon anchor 98 is initially positioned over selective region 150 and about distal lumen port 94. As best shown in FIG. 4C, opposed ends 154 and 156 of inflatable balloon anchor 98 are treated to a thermal welding procedure to hot weld opposed ends 154 and 156 to coating 152 on the distal end of elongated tube 88. In this manner, inflatable balloon anchor 98 is securely affixed to selective region 150 of elongated tube 88.

Referring to FIG. 4D, in a preferred embodiment, there is provided a silicone sleeve 158 which is configured to be positioned about inflatable balloon anchor 98. Silicone sleeve 158 is secured about inflatable balloon 98 by a pair of rings 160 and 162 which are positioned about opposed ends 164 and 166 of silicone sleeve 158. Preferably, rings 160 and 162 are formed of a heat shrinkable material such that when silicone sleeve 158 is positioned over inflatable balloon anchor 98 and heat shrink rings 160 and 162 are positioned about opposed ends 164 and 166 of silicone sleeve 158, rings 160 and 162 may be subjected to a heat treatment which will shrink rings 160 and 162 thereby securing silicone sleeve 158 over inflatable balloon anchor 98. The rings 160 and 162 serve to reinforce the balloon anchor 98 at its proximal and distal ends. The sleeve 158 may comprise a sleeve of any resilient, bio-compatible material. Furthermore, other methods may be used to attach the balloon anchor 98 to the tube 88, such as by adhering the balloon anchor 98 to the tube 88. In further alternatives, the balloon anchor 98 may be suture-tied to the balloon and coated with RTV.

Referring to FIG. 4, in a preferred embodiment, balloon tip cannula 82 further includes a skin seal 100 slidably attached to the outside of tube 88. Skin seal 100 desirably includes a foam collar 102 and a securing means 104 for securing the skin in a desired longitudinal position along longitudinal axis-x. A suitable skin seal is disclosed in International Publication No. WO02/096307 entitled Balloon Cannula with Over Center Clamp, the entire disclosure of which is hereby incorporated by reference herein. When balloon tip cannula 82 is inserted through an incision in the patient's skin, skin seal 100 is moved into position against the skin surface of the patient's body forming a pressure barrier, thereby minimizing the loss of inflation pressure through the opening in the patient's skin, and in combination with anchor balloon 98, secures balloon tip cannula 82 to the patient's body.

Balloon tip cannula 82 additionally includes an adapter flange 106 having proximal and distal openings defining a bore therebetween. On one surface of adapter flange 106 is a valve port 108 dimensioned to receive a valve 110 in a substantially fluid-tight sealing manner. The distal end of adapter flange 106 is dimensioned to receive and be affixed to the proximal end of cannula tube 88 in a substantially fluid-tight sealing manner. When the proximal end of cannula tube 88 is fully inserted in the distal end of adapter flange 106, valve port 108 is aligned with proximal lumen port 92, and thereby aligned with valve 110. Located near the proximal end of adapter flange 106 are a pair of recesses 112 each having a generally rectangular configuration and preferably diametrically opposed to one another. Recesses 112 are configured to receive a latching structure associated with obturator 128 as described hereinbelow. Alternatively, when used in combination with balloon dissector 12 as described hereinbelow, recesses 112 provide attachment points for latching adaptor 34. In other embodiments, no latching structure is used between the balloon dissector assembly 10 and balloon tip cannula assembly 80.

Balloon tip cannula 80 preferably employs a one-way check valve having a stopcock for inflating and deflating anchor 98. An anchor inflation valve 110 is preferably located on a surface of adapter flange 106 that is readily accessible during a surgical procedure. When anchor inflation valve 110 is attached to adapter flange 106, valve port 114 is aligned and in fluid communication proximal lumen port 92 and therefore in fluid communication with balloon anchor 98. Anchor inflation valve 110 also includes a valve handle 116 that is rotatably attached to anchor inflation valve 110 wherein internal valve ports (not shown) are configured to permit fluid flow between valve port 114 and proximal lumen port 92. In other embodiments, a separate deflation device may be provided.

In order to inflate balloon anchor 98, a source of inflation pressure is releasably attached to valve port 114. Valve handle 116 is rotated to align the internal valve ports for fluid flow through anchor inflation valve 110. Pressurized fluid is introduced through valve port 114 and is communicated through anchor inflation valve 110, proximal lumen port 92, and inflation lumen 96 to balloon anchor 98. Examples of preferred inflation fluids include $CO_2$, saline solution, or other biocompatible fluids. The pressurized fluid causes balloon anchor 98 to expand. In a preferred embodiment, anchor inflation valve 110 is a one-way check valve with a stopcock. Having a check-valve internal to anchor inflation valve 110 minimizes the loss of inflation pressure through anchor inflation valve 110 thereby allowing balloon anchor 98 to maintain its shape and inflation pressure. Advantageously, anchor inflation valve 110 includes a stopcock for releasing the inflation pressure. Including a stopcock with anchor inflation valve 110 allows the surgical personnel to have better control over the inflation and deflation of balloon anchor 98 since the stopcock is mounted on anchor inflation valve 110 where it is readily accessible to the surgical personnel. However, separate inflation and deflation devices may be provided on the balloon tip cannula.

An insufflation port 120 is provided on adapter flange 106 and in fluid communication with the interior of adaptor flange 106 and interior of tube 88 to provide insufflation fluid to the interior of a patient's body.

Seal assembly 84 generally includes a duckbill seal 122 configured and adapted to be received by the interior surface of adapter flange 106 wherein the outer surface of duckbill seal 122 and the interior surface of adapter flange 106 mate in a substantially fluid-tight sealing manner. Duckbill seal 122 functions in conventional manner to seal balloon tip cannula in the absence of an instrument having been inserted into the balloon tip cannula, and provide a seal against the escape of insufflation fluid. While duckbill seal 122 is shown closed in FIG. 3 with obturator 86 in place, it is to be understood that duckbill seal 122 would only be closed in the absence of an instrument therethrough. An opening is located at the proximal end of duckbill seal 122 for receiving an adapter ring 124. Adapter ring 124 is sized for snug engagement with duckbill seal 122 and includes a substantially central orifice dimensioned to receive a surgical device, such as an obturator and provides a seal around such surgical device. Further still, adapter ring 124 is maintained in position within the proximal region of duckbill seal 122 by a retainer ring 126 having a central opening substantially equal to the opening of adapter ring 124. A reducing device as described hereinabove with respect to balloon dissector 12 may be included as well to accommodate various diameter instruments. The reducing device is attached to retainer ring 126 for slidably engaging tubular surgical devices of differing sizes and providing a degree of stability for the surgical devices inserted through retainer ring 126. Although the duckbill seal 122 and ring 124 are shown in this embodiment, other embodiments include seals having different configurations. Desirably, the balloon tip cannula assembly 80 include both a seal for sealing the interior of tube 88 in the absence of instruments that may be received in the assembly, as well as a seal for sealing against an instrument, once inserted into the assembly.

Balloon tip cannula assembly 80 further includes obturator 86 for facilitating insertion of balloon tip cannula through an incision in a patient's body. Obturator 86 generally includes a obturator body 128, a cap 130 affixed to obturator body 128 and a latching adapter 132 affixed to cap 130 and surrounding obturator body 128. In further embodiments, the latching adapter 132 is eliminated and latches are incorporated on cap 130. Obturator body 128 is generally elongate and cylindrical and has a rounded obturator tip 134 located at the distal end of obturator body 128. Obturator body 128 includes an obturator adapter 136 disposed at its proximal end.

Latching adapter 132 is attached to cap 130 in a manner similar to that described above with respect to the latching adapter of balloon dissector 12. Obturator adaptor 136 is affixed to an inner surface of cap 130. Latching adapter 132 is generally circular in configuration having a throughbore. A plurality of resilient tabs 138 are located at the distal end, each tab 138 being separated from each other tab by a slot. In addition, each tab 138 is biased towards the center of the throughbore for engagement with cap 130 in a manner similar to that discussed above with respect to latching adapter 34 and end cap 30. Located near the proximal end of latching adapter 132 is a pair of diametrically opposed arms 140. Each arm 140 is pivotably attached to latching adapter 132 whereupon each arm 140 rotates about a pivot point substantially perpendicular to longitudinal axis-x. Preferably, each arm 140 is biased in a starting position, is capable of rotation away from the other arm, and includes a hook 142 at its distal end wherein each hook 142 is configured to releasably mate with recess 112 of adapter flange 106.

When obturator 86 is inserted and advanced along longitudinal axis-x through retaining ring 126, adapter ring 124, duckbill seal 122, and through tube 88, latching adapter 132 is advanced distally and hooks 146 approach and engage recesses 112. Preferably, the arms 140 are biased toward a latching position and deflect inwardly, then snap into engagement with recesses 112. The operator may rotate arms 140 by moving levers 144 in a generally outward direction, thereby causing hooks 142 to rotate generally inwards. After obturator 86 is fully inserted into balloon tip cannula 82, the operator releases levers 144, thereby allowing arms 140 to return their starting position. In the starting position, hooks 142 engage recesses 112 to retain latching adapter 132 and obturator 86 in position. In addition, when the assembled structure is fully inserted, obturator tip 134 extends beyond the distal end of tube 88.

Cap 130 includes a pair of grooves 146 configured and adapted for slidably receiving arms 140. It is preferred that cap 130 be configured for ergonomic efficiency whereby the operator can use cap 150 with a minimum of effort or discomfort.

In certain preferred embodiments, the cap 130, latching adapter 132 and obturator body 128 may be combined in a unitary structure. The obturator body 128 may be provided with a proximal end without latching engagement with the adapter flange 106.

A method of using balloon tip cannula assembly 80 is disclosed. An incision is made in the skin of the patient in the area of interest. Using the assembled balloon tip cannula assembly 80, the surgeon advances obturator tip 134 and the distal end of balloon tip cannula assembly 80 into the incision, thereby positioning balloon tip cannula assembly 80 into the area of interest.

Once balloon tip cannula assembly 80 is positioned, inflation fluid is applied through valve port 114 and valve port 108 thereby communicating the inflation pressure to proximal lumen port 92. Since proximal and distal lumen ports 92, 94 are in direct fluidic communication with each other through inflation lumen 96, inflation fluid is transferred to distal lumen port 94 and therefore to balloon anchor 98. As inflation fluid is applied to balloon anchor 98, it expands to reach its predetermined shape. After the anchor balloon 98 is expanded, it abuts the underside of the patient's skin to hold balloon tip cannula assembly 80 in position. Preferably, balloon anchor 98 has a shape for anchoring the balloon tip cannula assembly 80, such as the toroidal shape shown and is of sufficient size to hold cannula 80 in a desired position. It is contemplated that the balloon anchor may have any other shape.

After balloon tip cannula assembly 80 is located through the incision and balloon anchor 98 expanded, skin seal 100 is advanced distally along cannula tube 88 until it is in an abutting relationship with the outer surface of the patient's body such that foam collar 102 is compressed and means for securing 104 the skin seal 100 are actuated to lock skin seal against cannula tube 88.

Once balloon tip cannula assembly 80 is anchored in position, levers 144 are rotated outwards causing arms 140 to rotate inwards, thereby disengaging hooks 142 from recesses 112. After hooks 142 are disengaged from recesses 112, obturator 86 is retracted from balloon tip cannula 82 while the surgeon holds balloon tip cannula 82 in position, thereby separating the components. After obturator 86 is completely removed, other surgical structures may be installed in balloon tip cannula 82 to access the surgical site. Examples of such surgical instruments include, but are not limited to, endoscopes, graspers, shears, surgical suturing devices, and surgical device applicators.

Upon completion of the surgical procedure, the surgeon deflates anchor balloon 98 by operating valve 110. Inflation pressure held by anchor balloon 98 exits the system through valve port 114 by reversing the flow path for inflation. Once anchor balloon 98 is sufficiently deflated, balloon tip cannula 92 is removed from the surgical site. The silicone sleeve over the anchor balloon 98 resiliently applies pressure against the balloon, tending to deflate the balloon as the valve is opened. After removal, the incision may be sutured closed, or other surgical structures may be used at the incision site for additional surgical procedures.

Figure 5:
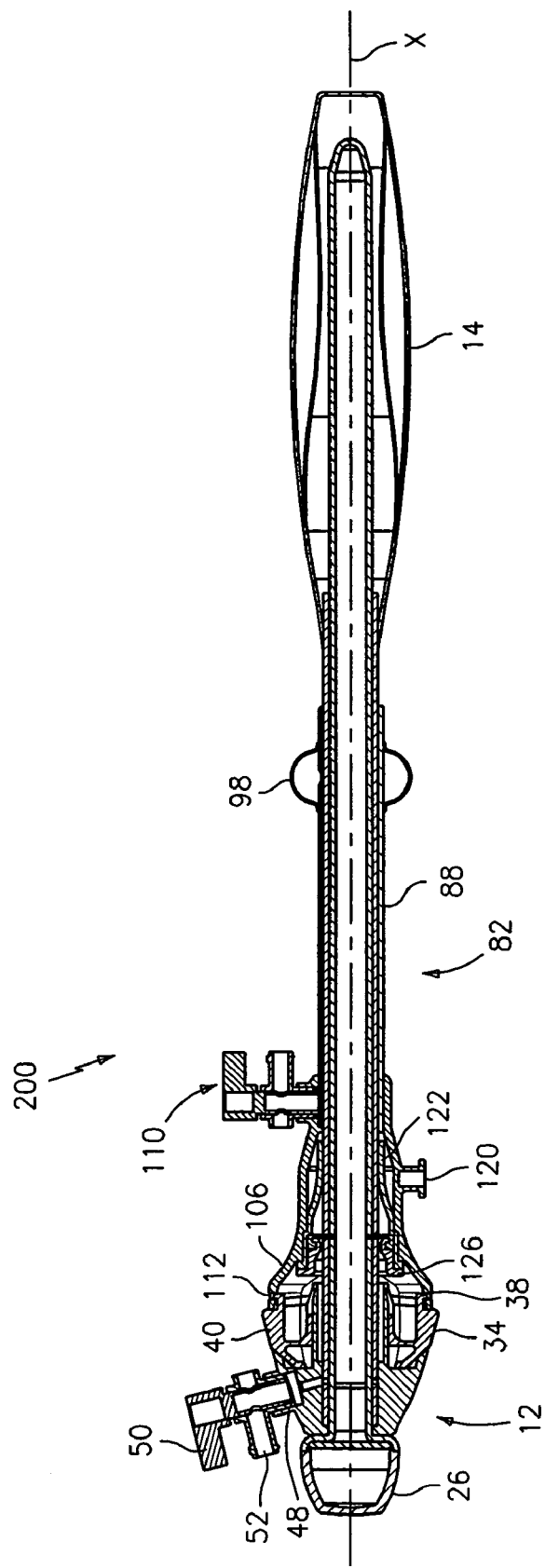
FIG. 5 is a cross-sectional side view of a combined balloon dissector with balloon tip cannula according to a further embodiment of the present invention.
Figure 6:
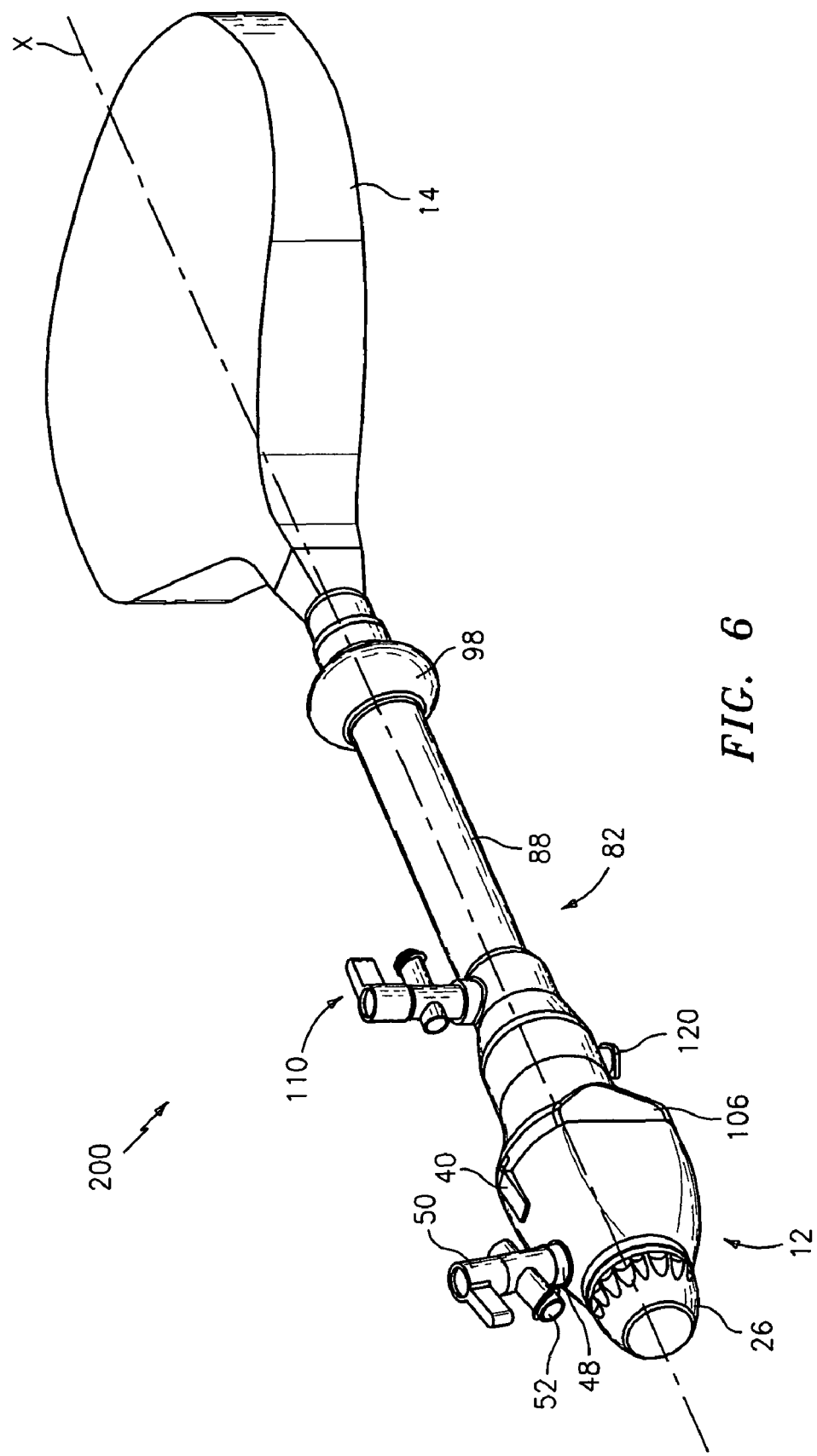
FIG. 6 is a perspective view of the combined balloon dissector with balloon tip cannula in accordance with the embodiment of FIG. 5.

Referring now to FIGS. 5 and 6, and as noted above, balloon dissector assembly 10 and balloon tip cannula 80 can be used separately as individual instruments in the manner described hereinabove or preferably, and more advantageously, can be combined together to form a combined balloon dissector with balloon tip cannula 200. This allows the surgeon to eliminate operational steps when creating an anatomical space within a body. Balloon dissector with balloon tip cannula 200 includes components of balloon dissector above and balloon tip cannula above. Each of these instruments are designed so as to be easily combined into a single instrument.

Referring now to FIGS. 5 and 6, the combined assembly 200 has the balloon dissector 12 and obturator assembly 26 inserted through retaining ring 126 and duckbill valve 122 of the balloon tip cannula 82 such that dissection balloon 14 and dissector tube 18 are advanced through cannula tube 88 of balloon tip cannula 82. The balloon dissector 12 desirably has a latching adapter 34 that engages recesses 112 in an adapter body 106 of balloon tip cannula 82 to securely lock balloon dissector 12 to balloon tip cannula 82. However, in other embodiments, no connecting structure is provided. Once assembled, the combined balloon dissector with balloon tip cannula 200 is ready to be used to create an anatomical space within a body cavity within a patient's body and provide a secured access port for receipt of surgical instruments.

In use, an initial incision is made through the abdominal wall of a patient's body. The combined balloon dissector with balloon tip cannula 200 is positioned such that dissection balloon 14, supported by obturator assembly 26, is inserted through the incision. The combined device is advanced through the incision until dissection balloon 14 is at a desired location. At this point, obturator assembly 26 may be removed and a endoscope inserted therein.

Once in a proper position, a source of inflation fluid is connected to valve port 52 of dissector inflation valve 50 and inflation fluid is forced through connecting port 48 and the lumen 23 defined by the inner surface of tube 18 and the outer surface of obturator 26. The inflation pressure forces dissector balloon 14 to start to expand which forces perforations 21 of sleeve cover 60 (FIG. 2) to separate to thereby release the balloon. As noted above, the balloon is typically in a rolled up configuration and as it unfurls it unrolls or unfolds laterally and expands vertically relative to the plane of the balloon to separate tissue layers along natural tissue planes to form an anatomical space for a surgical procedure.

Once the tissue has been dissected and the anatomical space formed, dissection balloon 14 can be deflated by opening dissector inflation valve 50 to release the inflation pressure or by removing obturator assembly 26 thereby opening the adapter orifice 46 to the inflation lumen 23, which is defined between obturator 26 and the inner surface of dissector tube 18. Once balloon 14 has been deflated, the balloon dissector assembly 10 is disconnected from the balloon tip cannula 82 by depressing levers 40 thereby releasing hooks 38 on latching adaptor 34 from recesses 112 in adapter body 106. The balloon tip cannula 82 is slid down the tube 18 of balloon dissector assembly 10 and the balloon tip cannula 82 is advanced through the incision to position balloon anchor 98 within the abdominal wall. A source of inflation fluid is connected to valve 110 to inflate balloon anchor 98. Once balloon anchor 98 has been inflated, the user applies a slight proximal tension on the combined device so as to draw anchor balloon against the inner surface of the abdominal wall. The skin seal 100 (FIG. 4) is slid distally along cannula tube 88 to compress foam 102 against an outer surface of abdomen and, upon actuating the securing means 104 of skin seal 100, cannula 82 is securely locked to the abdominal wall, sealing the incision against escape of insufflation fluid.

The balloon dissector assembly 10 is then removed from balloon tip cannula 82. Once balloon dissector has been removed, duck bill valve 122 is in a closed position to form a seal in the proximal end of balloon tip cannula 82. Thereafter, a source of insufflation fluid is connected to insufflation port 120 and fluid forced through balloon tip cannula 82 into the body to insufflate and expand the space. Once a space has been created with the insufflation fluid, additional instruments including endoscopes, graspers, tackers, staplers, etc. may be inserted through balloon tip cannula to perform an operation such as, for example, a hernia repair procedure, within a patient.

In alternative embodiments, the obturator assembly 26 may be removed, either before or after the balloon dissector assembly 10 is introduced into the body, and an endoscope may be inserted into the dissector tube 18 prior to or after inflation of the dissection balloon.

Once a procedure has been completed, insufflation fluid is withdrawn from the body through insufflation port 120 and anchor inflation valve 110 is opened to allow the inflation fluid to exit from anchor balloon 98. The silicone sleeve of the anchor balloon 98 provides pressure tending to deflate the anchor balloon 98. Balloon tip cannula 82 is then removed through the incision and the incision and the incision is closed in a normal manner.

Prior art dissection methods generally include inserting a first device, typically a type of dissector, into the patient through an incision at the surgical site whereupon the surgical personnel will dissect the separated tissues. Then a second device, typically a trocar cannula is used to insufflate, maintaining a working space.

Using a combination device including a balloon tip cannula 82 and a balloon dissector 12 minimizes the number of procedural steps required to dissect and insufflate. Furthermore, the balloon tip cannula 82 includes a skin seal and balloon anchor for anchoring the balloon tip cannula 82 and sealing the incision. Ports for inflating the dissection balloon 14 and balloon anchor 98 are provided. The balloon anchor 98 is easily deflated, as the sleeve 158 biases the balloon 98 towards deflation. Separate deflation mechanisms are not required, but may be provided. The combined device 200 includes a passage for receiving an endoscope so that dissection may be observed.

Figure 7:
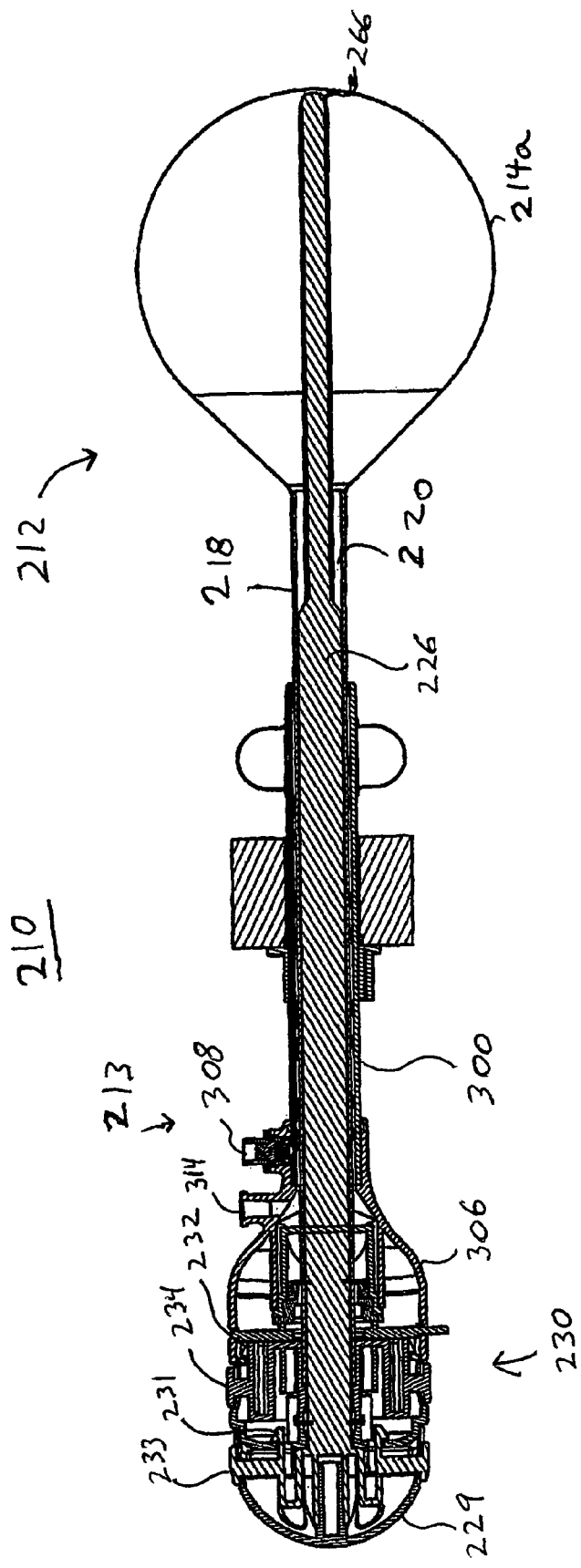
FIG. 7 is a cross-sectional view of a further embodiment of a combined balloon dissector and balloon tip cannula.
Figure 8:
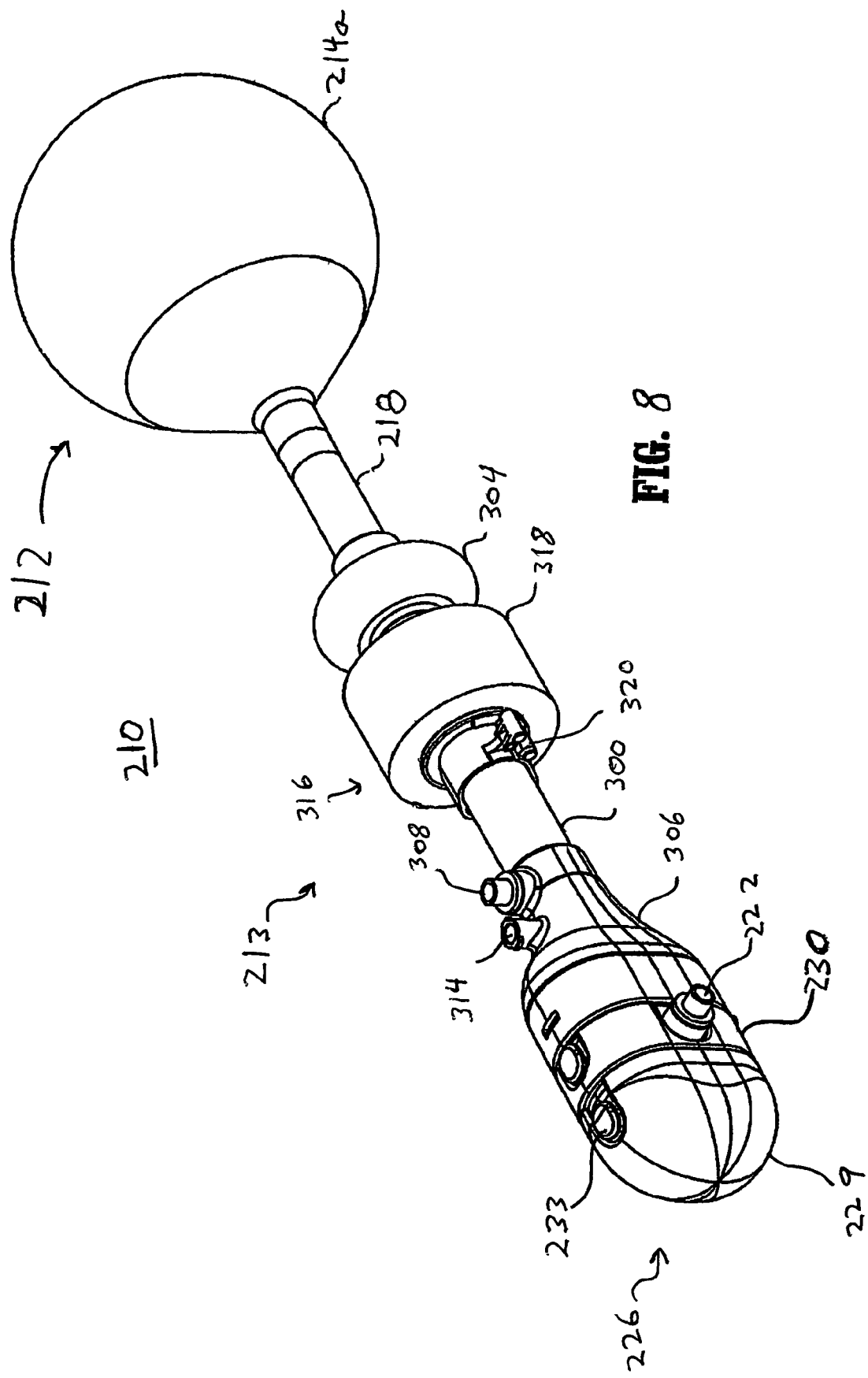
FIG. 8 is a perspective view of the combined balloon dissector and balloon tip cannula in accordance with the embodiment of FIG. 7.

Referring to FIGS. 7 and 8, an alternate embodiment of a balloon dissector and cannula assembly 210 is shown and has a balloon dissector assembly 212 and a balloon tip cannula assembly 213. Balloon dissector assembly 212 has an elongated tube 218 having a distal end and a proximal end and defining a passage 220. A dissection balloon 214a is affixed to the distal end of tube 218. Dissection balloon 214a forms a chamber that communicates with passage 220. Dissection balloon 214a is round and expands to a shape that follows the path of least resistance in tissue. The dissection balloon 214a may have other shapes, such as oblong, kidney shaped, etc.

Figure 9:
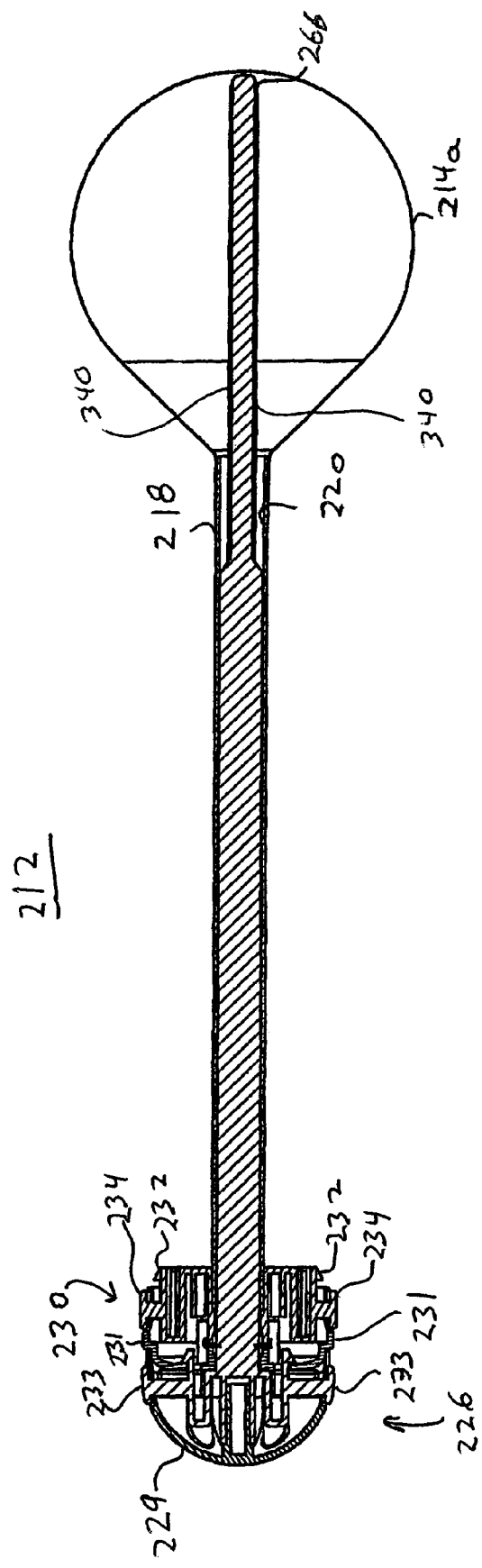
FIG. 9 is a cross-sectional view of the balloon dissector in accordance with the embodiment of FIG. 7.

Referring to FIGS. 8 and 9, a dissector housing 230 is formed on the proximal end of tube 218. The dissector housing 230 has an orifice at a proximal end and includes a seal. Dissector housing 230 may be formed of two parts to support the seal. Dissector housing 230 defines an inflation port 222 dimensioned for receiving a one-way inflation valve. The inflation valve and inflation port 222 communicate with dissection balloon 214a through tube 218.

An obturator 226 having a distal tip 266 is received through the orifice in the dissector housing 230, through passage 220 in tube 218, and into the chamber of dissection balloon 214a. The outer surface of obturator 226 and the inner surface of tube 218 form an inflation lumen between inflation port 222 and dissection balloon 214a. The proximal end of obturator 226 has a cap 229 which carries resilient latches 231 connected to buttons 233. When obturator 226 is received in dissector housing 230 and advanced into tube 218, distal tip 266 engages dissection balloon 214a and supports it in a collapsed, elongated shape (not shown). The latches engage recesses on dissector housing 230. Additional latches 232, connected to buttons 234, are provided on dissector housing 230 for interconnecting dissector housing 230 to cannula housing 306 of balloon tip cannula assembly 213.

In order to inflate dissection balloon 214a, a source of inflation pressure is releasably attached to inflation port 222 and pressurized fluid is introduced through inflation port 222 and communicated through inflation tube 218 to dissection balloon 214a.

Figure 10:
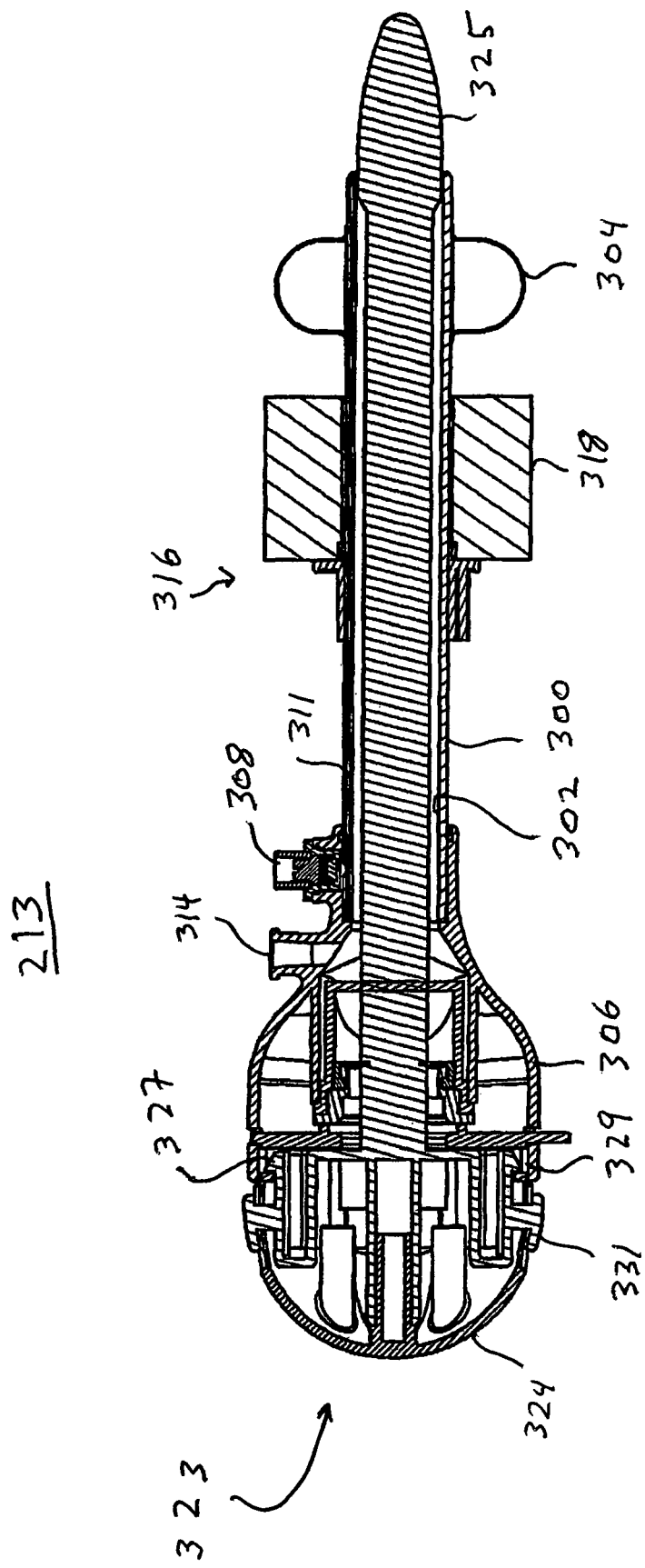
FIG. 10 is a cross-sectional view of the balloon tip cannula in accordance with the embodiment of FIG. 7.

Referring to FIGS. 8 and 10, balloon tip cannula assembly 213 has a cannula 300 which is open at its proximal and distal ends to define an access lumen 302 for receipt of surgical instruments therethrough. An inflatable balloon anchor 304, having a generally toroidal shape, is disposed in the distal region of cannula 300. As with prior embodiments, the balloon anchor 304 is formed by dipping the cannula into a urethane coating and then using thermal welding to attach a urethane membrane to the coated cannula. The membrane is then coated with RTV and heat shrink tube collars reinforce the sleeve at the welded ends. Alternatively, the balloon anchor 304 may be attached as discussed above in connection with FIGS. 4A-4D.

A cannula housing 306 is attached to cannula 300 at a proximal end of cannula 300. Cannula housing 306 has an orifice that communicates with access lumen 302. A valve port 308 is provided in a surface of cannula housing 306. Valve port 308 is dimensioned to receive a check valve in a substantially fluid-tight sealing manner. An inflation lumen 311 is defined between the inner surface and the outer surface of cannula 300 and extends to balloon anchor 304. The check valve communicates with balloon anchor 304, through the lumen in the wall of the cannula.

In order to inflate balloon anchor 304, a source of inflation pressure is releasably attached to the check valve, introducing pressurized fluid through valve port 308 to balloon anchor 304, which causes balloon anchor 304 to expand.

An insufflation port 314 is also provided on cannula housing 306, and in fluid communication with the interior of cannula housing 306 and cannula 300, to provide insufflation fluid to the interior of a patient's body.

A seal assembly is provided in the cannula housing 306 for sealing the interior of cannula 300 during insufflation. The seal assembly generally includes a seal for sealing around instruments inserted into cannula 300 and a seal for sealing cannula 300 in the absence of any instruments inserted into cannula 300. These seals may be the seals discussed above in connection with FIG. 3.

A skin seal 316 is slidably mounted on the outside surface of cannula 300. Skin seal 316 includes a compressible foam collar 318 and a clamp 320 for securing the skin seal in a desired longitudinal position along the cannula. The skin seal 316 may be as discussed above in connection with FIG. 4.

Referring to FIG. 10, an obturator 323 having a proximal cap 324 and a distal end 325 is inserted in the orifice of cannula housing 306, and advanced through lumen 302 of cannula 300, so that distal end 325 extends out of the distal end of cannula 300. Cannula housing 306 has recesses 329 for receiving latches 327 on proximal cap 324 of obturator 323. Proximal cap 324 also carries buttons 331 for disengaging the latches. To assemble the balloon dissector assembly 212 and balloon tip cannula assembly 213, obturator 323 is removed from cannula 300. Balloon dissector assembly 212 is inserted into the orifice of cannula housing 306 and advanced through lumen 302 of cannula 300 so that latches 232 on dissector housing 230 are engaged with cannula housing 306, interconnecting the assemblies.

The balloon dissector assembly 212 is used for dissecting tissue along natural tissue planes in general, laparoscopic, vascular, endoscopic, plastic or reconstructive surgery. A suitably sized incision is made in the patient's skin. Next, the assembled balloon dissector and cannula assembly 210 is inserted into the incision, using the obturator 226 to tunnel a passage beyond the point of incision.

Inflation pressure is supplied through inflation port 222 from a suitable outside source and is communicated to dissection balloon 214a. As pressure is applied, dissection balloon 214a expands. The expansion of dissection balloon dissects surrounding tissue along natural tissue planes. Once the desired space is created, dissection balloon 214a is deflated by removal of obturator 226 which allows the inflation pressure to be relieved through the orifice in the dissector housing 230.

In an alternative method, obturator 226 is removed from tube 218 and replaced with an endoscope. Then, balloon dissector assembly 212 is inserted into the skin incision and dissector balloon 214a is inflated as discussed above. The scope is used for viewing the dissected space and for viewing during dissection. The endoscope may be inserted into tube 218 before or after dissection.

After dissection balloon 214a is deflated, cannula housing 306 is unlatched from dissector housing 230 by pressing buttons 234 on dissector housing 230. Cannula 300 is advanced along balloon dissector tube 218 and positioned within the incision so that balloon anchor 304 is located inside the body cavity. Inflation fluid is supplied through valve port 308 thereby communicating the inflation fluid to balloon anchor 304 at the distal end of cannula 300, expanding balloon anchor 304. After anchor balloon 304 is expanded, it is brought into engagement with the underside of the patient's abdominal wall.

Skin seal 316 is moved into position against the surface of the patient abdominal wall and secured using the clamp. Skin seal 316 forms a pressure barrier, thereby minimizing the loss of insufflation pressure through the opening in the patient's abdominal wall and, in combination with anchor balloon 304, secures balloon tip cannula 300 to the patient's body.

Balloon dissector assembly 212 is removed from cannula 300 and surgical instruments are introduced to the surgical site through cannula 300. Examples of such surgical instruments include, but are not limited to, endoscopes, surgical suturing devices, and surgical manipulation devices, etc.

Upon completion of the surgical procedure, the surgeon deflates anchor balloon 304 by releasing the check valve attached to valve port 308. Once anchor balloon 304 is sufficiently deflated, cannula 300 is removed from the incision.

The balloon dissector assembly 212 may be provided with a second type of dissection balloon which is a laterally extending oval balloon. The oval balloon and/or round balloon may comprise an elastic or inelastic material. The elastic material will tend to follow the path of least resistance in the patient's body, whereas the inelastic balloon tends to expand to a predetermined shape. The selection of the type of balloon is left up to the surgeon.

The oval dissection balloon 214b desirably has an initial collapsed configuration, with the lateral margins of balloon 214b rolled inwardly toward obturator 226 of balloon dissector assembly 212, similar to the rolled configuration discussed above in connection with FIG. 2A. Obturator 226 desirably has two recessed flats 340, one on each of the lateral sides of obturator 226, for accommodating the rolled margins of balloon 214b (FIG. 9). A sleeve (not shown) is provided around dissection balloon 214b to retain dissection balloon 214b in a collapsed condition during insertion into the body and prior to inflation. The sleeve comprises a sheet of polymeric material that may be attached to the material of the balloon 214b, as discussed above. The sleeve includes a longitudinal weakened perforated region such that, upon inflation of dissection balloon 214b, the sleeve separates along the perforations and releases dissection balloon 214b. As the balloon is inflated, the balloon unrolls or unfolds in a lateral direction with respect to the tube 218.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A surgical instrument comprising:
   a balloon tip cannula assembly, including:
     a cannula housing,
     a cannula tube extending distally from the cannula housing, the cannula housing having a balloon anchor at a distal end of the cannula tube, and
     a skin seal movable along the cannula tube;
   a balloon dissector assembly configured to be received through a proximal opening of the balloon tip cannula assembly, the balloon dissector assembly being engageable and disengageable from the balloon tip cannula assembly, the balloon dissector assembly including:
     a dissector housing,
     a dissector tube including a proximal end, the dissector tube extending distally from the dissector housing, and
     a dissection balloon mounted on a distal end of the dissector tube;
   an obturator having a distal tip configured to be received through proximal openings of the balloon tip cannula assembly and the balloon dissector, the distal tip of the obturator supporting and contacting the dissection balloon, the obturator being separable and removable from the balloon tip cannula assembly prior to and after inflation of the dissection balloon; and
   one of the dissector housing and cannula housing including a latching structure having a latch, and the other of the dissector housing and cannula housing having a recess for receipt of the latch of the latching structure, wherein the cannula housing and the dissector housing are releasably coupled to one another.

2. The surgical instrument as recited in claim 1, wherein the latching structure includes at least one movable arm.

3. The surgical instrument as recited in claim 2, wherein the at least one movable arm include a hook engageable with the recess.

4. The surgical instrument as recited in claim 1, further comprising:
   an adapter assembly configured for attachment to the proximal end of the dissector tube, the adapter assembly including:
   a shroud, the shroud removably attachable to the cannula housing, the shroud being configured and adapted to surround the proximal end of the dissector tube;
   a latching adapter; and
   an end cap,
   wherein any of the end cap, latching adapter, and shroud are combinable, and wherein any of the end cap, latching adapter, and shroud are removable from one another.

5. The surgical instrument as recited in claim 1, further comprising an end cap removably attachable to the dissector housing.

6. The surgical instrument as recited in claim 1, further comprising a sleeve surrounding at least a portion of the balloon anchor, the sleeve tending to bias the balloon anchor towards deflection, the cannula housing having a valve in communication with the balloon anchor.

7. The surgical instrument as recited in claim 6, wherein the anchoring balloon is formed of urethane material.

8. The surgical instrument as recited in claim 6, further comprising a ring positioned about each opposed end of the sleeve.

9. The surgical instrument as recited in claim 8, wherein each ring is formed of a heat shrinkable material.

10. The surgical instrument as recited in claim 1, wherein the balloon dissector assembly and the obturator are separately attachable to the balloon tip cannula assembly.

11. The surgical instrument of claim 1, wherein the obturator supports and contacts the dissection balloon in a collapsed state.

12. A surgical instrument comprising:
- a balloon tip cannula assembly, including:
  - a cannula housing having a cannula tube extending therefrom, the cannula tube having a balloon anchor disposed at one end thereof, and
  - a skin seal movable along the cannula tube;
- a balloon dissector assembly configured to be received through a proximal opening of the balloon tip cannula assembly, the balloon dissector assembly being engageable and disengageable from the balloon tip cannula assembly, the balloon dissector assembly including:
  - a dissector housing;
  - a dissector tube including a proximal end, the dissector tube extending distally from the dissector housing, and
  - a dissection balloon mounted on one end of the dissector tube;
- an obturator configured to be received through proximal openings of the balloon tip cannula assembly and the balloon dissector assembly, at least a portion of the obturator supporting and contacting the dissection balloon, the obturator being engageable and disengageable from the balloon tip cannula assembly prior to and after inflation of the dissection balloon; and
- an adapter assembly configured for attachment to the proximal end of the dissector tube, the adapter assembly including:
  - a shroud, the shroud removably attachable to the cannula housing, the shroud being configured and adapted to surround the proximal end of the dissector tube, a latching adapter, and an end cap, wherein any of the end cap, latching adapter, and shroud are combinable, and wherein any of the end cap, latching adapter, and shroud are removable from one another,
- wherein one of the dissector housing and cannula housing including a latching structure having a latch, and the other of the dissector housing and cannula housing having a recess for receipt of the latch of the latching structure, wherein the cannula housing and the dissector housing are releasably coupled to one another.

13. The surgical instrument of claim 12, wherein the obturator supports the dissection balloon in a collapsed state.

14. The surgical instrument of claim 12, wherein a distal portion of the obturator supports and contacts the dissection balloon.

* * * * *